(12) United States Patent
Ebisu et al.

(10) Patent No.: US 11,952,398 B2
(45) Date of Patent: *Apr. 9, 2024

(54) CHROMATOGRAPHIC METHOD FOR COLLECTING BLOOD COAGULATION FACTOR VII WITH HIGH YIELD

(71) Applicant: KM Biologics Co., Ltd., Kumamoto (JP)

(72) Inventors: Kentaro Ebisu, Koshi (JP); Takashi Kai, Koshi (JP); Nozomi Matsuo, Kumamoto (JP)

(73) Assignee: KM Biologics Co., Ltd., Kumamoto (JP)

( * ) Notice: Subject to any disclaimer, the term of this patent is extended or adjusted under 35 U.S.C. 154(b) by 127 days.

This patent is subject to a terminal disclaimer.

(21) Appl. No.: 17/342,928

(22) Filed: Jun. 9, 2021

(65) Prior Publication Data

US 2021/0292359 A1 Sep. 23, 2021

Related U.S. Application Data

(62) Division of application No. 16/471,830, filed as application No. PCT/JP2017/045680 on Dec. 20, 2017, now Pat. No. 11,059,857.

(30) Foreign Application Priority Data

Dec. 22, 2016 (JP) ................. 2016-249815

(51) Int. Cl.
*C07K 1/18* (2006.01)
*A61K 38/36* (2006.01)
*C07K 1/22* (2006.01)

(52) U.S. Cl.
CPC ............... *C07K 1/18* (2013.01); *A61K 38/36* (2013.01)

(58) Field of Classification Search
CPC ............ A61K 38/36; C07K 1/22; C07K 1/18
See application file for complete search history.

(56) References Cited

U.S. PATENT DOCUMENTS

| 5,700,914 A | 12/1997 | Jørgensen et al. |
| 6,395,880 B1 | 5/2002 | Linnau |
| 6,777,390 B1 | 8/2004 | Matthiessen et al. |
| 10,723,761 B2 * | 7/2020 | Mitterer ............... C07K 14/473 |
| 2014/0302591 A1 | 10/2014 | Mitterer |
| 2017/0073396 A1 | 3/2017 | Bataille et al. |

FOREIGN PATENT DOCUMENTS

| JP | 3-155797 | 7/1991 |
| JP | 8-508264 | 9/1996 |
| JP | 10-59866 | 3/1998 |
| JP | 2002-518411 | 6/2002 |
| JP | 2008-275423 | 11/2008 |
| JP | 2016-109468 | 6/2016 |
| WO | 2013/053888 | 4/2013 |
| WO | 2015/136217 | 9/2015 |

OTHER PUBLICATIONS

International Search Report dated Mar. 20, 2018 in International Application No. PCT/JP2017/045680.
International Preliminary Report on Patentability dated Jan. 28, 2019 in International Application No. PCT/JP2017/045680.
Tomokiyo et al, "Large-scale production and properties of human plasma-derived activated Factor VII concentrate", Vox Sanguinis, 2003, vol. 84, pp. 54-64.
Hedner et al., "Use of human factor VIIa in the treatment of two hemophilia A patients with high-titer inhibitors", J. Clin. Invest. 71, pp. 1836-1841, (1983).
Wildgoose et al., "Measurement of Basal Levels of Factor VIIa in Hemophilia A and B Patients", Blood, 80, pp. 25-28, (1992).
H. Prydz, "Studies in Proconvertin (Factor VIII) II. Purification", J. Scand. J. Clin. Lab. Invest. 1, pp. 101-107, (1964).
Gladhaug et al., "Purification of the Coagulation Factors VII and X From Human Serum Some Properties of Factor VII", Biochim. Bioplys. Acta 215, pp. 105-111, (1970).
Laake et al., "Purification and Some Characteristics of Factor VII in Human Citrated Plasma, Glass-Activated Serum, and Cold-Activated Plasma", Thromb. Res. 5, pp. 539-556, (1974).
Schiffman et al., "Effect of Intermediates of Extrinsic Clotting on Purified Factor XI: Factor VII and/or Thromboplastin", Thromb. Res. 6, pp. 273-279, (1975).
Østerud et al., "Activation of Factor IX by the reaction product of tissue factor and Factor VII: Additional pathway for initiating blood coagulation", Proc. Natl. Acad. Sci. U.S.A. 74, pp. 5260-5264, (1977).
Broze et al., "Purification and Properties of Human Coagulation Factor VII", J. Biol. Chem. 255, pp. 1242-1247, (1980).
Production of Plasma Proteins for Therapeutic Use, p. 68 (2013) by John Wiley & Sons, Inc., Hoboken, New Jersey.
Extended European Search Report dated Jul. 17, 2020 in corresponding European Patent Application No. 17884308.2.
Josic et al., "Preparation of vitamin K-dependent proteins, such as clotting factors II, VII, IX and X and clotting inhibitor Protein C", Journal of Chromatography B, 2003, vol. 790, pp. 183-197.

* cited by examiner

*Primary Examiner* — Maryam Monshipouri
(74) *Attorney, Agent, or Firm* — Wenderoth, Lind & Ponack, L.L.P.

(57) ABSTRACT

A chromatographic method for collecting blood coagulation factor VII (Factor VII) and/or activated blood coagulation factor VII (activated Factor VII) from plasma-derived fractions with high yield is provided. In accordance with the method of the present invention, Factor VII and/or activated Factor VII of interest can be collected with a recovery rate of as high as 90% or more by letting Factor VII and/or activated Factor VII which fails to be adsorbed to a first anion exchange resin and remains in a non-adsorption fraction be adsorbed in a second anion exchange resin.

5 Claims, No Drawings

CHROMATOGRAPHIC METHOD FOR COLLECTING BLOOD COAGULATION FACTOR VII WITH HIGH YIELD

TECHNICAL FIELD

The present invention relates to a method for collecting blood coagulation factor VII (Factor VII) and/or activated blood coagulation factor VII (activated Factor VII) from plasma-derived fractions with high yield.

BACKGROUND ART

Blood coagulation consists of processes of complex interactions of various blood components or factors to finally generate fibrin clot. In general, for the blood components that participate in the reaction called blood coagulation cascade, there are two independent systems with which normal hemostasis is pertained, these systems being called "intrinsic pathway" and "extrinsic pathway".

Intrinsic pathway is a reaction pathway in which thrombin formation is introduced via those factors which are present in plasma alone. Intermediate phenomenon of said pathway is the activation of Factor IX (hereinafter also referred to as "FIX") catalyzed by activated Factor XI (hereinafter also referred to as "FXIa") and calcium ions. Then, activated Factor IX (hereinafter also referred to as "FIXa") is involved in the activation of Factor X (hereinafter also referred to as "FX") in the presence of activated Factor VIII (hereinafter also referred to as "FVIIIa"), phospholipids and calcium ions.

Extrinsic pathway is a reaction pathway in which plasma factors and factors present in tissue extracts are involved. One of blood coagulation factors, Factor VII (hereinafter also referred to as "FVII"), after being converted into activated Factor VII (hereinafter also referred to as "FVIIa"), participates in extrinsic pathway by activating FX to FXa in the presence of tissue factors and calcium ions. FXa then converts prothrombin into thrombin in the presence of activated Factor V (hereinafter also referred to as "FVa"), calcium ions and phospholipids. The generated thrombin acts to convert fibrinogen into fibrin so as to close the site of vascular injury, resulting hemostasis.

When these factors in blood coagulation cascade are deficient or do not normally function, blood coagulation becomes obstructed and bleeding symptoms are often shown. Most of them are caused by genetic predisposition. As typical diseases caused by congenital coagulation factor disorder, hemophilia A with deficiency of FVIII and hemophilia B with deficiency of FIX are well known. For the treatment of patients suffering from these hemophilia, pharmaceutical preparations comprising FVIII or FIX have been developed for the replacement of deficient factors and used for hemostatic management. This is called replacement therapy. However, as a consequence of this therapy, antibodies (inhibitors) against FVIII or FIX are known to be generated. When inhibitors are generated, the conventional replacement therapy becomes non effective, making hemostatic management of patients quite difficult.

For the treatment of hemophilia patients having inhibitors, the treatment with activated prothrombin complex concentrate has been conducted which is known to consist of a mixture of activated coagulation enzymes, including FVIIa, and inert coagulation enzymes. In recent years, it has been elucidated that a single active ingredient preparation of FVIIa is effective for suppressing severe progressive bleeding of hemophilia patients having a high level of anti-FVIII antibodies in plasma and thus FVIIa preparations have been used (Non-patent reference 1).

FVII is a single-stranded glycoprotein and is one of vitamin K dependent coagulation factors, which, in addition to FVII, consist of prothrombin, FIX, FX, protein C, protein S, and protein Z and are called prothrombin family due to high structural homology. FVII is mainly biosynthesized in the liver. It is known that FVII is present in human plasma as a precursor FVII, about 1% of which is present as FVIIa (Non-patent reference 2). FVII is a physiologically important protein that forms a complex with Tissue Factor and is responsible for the initiation reaction of blood coagulation. On the other hand, FVIIa is a double-stranded glycoprotein formed after restricted decomposition at the Arg152-Ile153 linkage of FVII. FVIIa is known to have a coagulation activity 25-fold higher than that of FVII and is useful for the treatment of hemophilia patients having antibodies against FVIII and FIX for which hemostatic management has hitherto been thought to be difficult as mentioned above.

As mentioned above, since FVIIa preparations are effective for the treatment of hemophilia patients having inhibitors, various methods have been attempted in order to prepare plasma-derived FVII. However, these methods for preparation could only attain partial purification of FVII but could not have succeeded in isolation of FVII per se as a pure substance (Non-patent references 3 to 5).

Under the circumstances, it is reported that FVII could be well prepared by a purification method comprising adsorption treatment with valium chloride and salting-out with ammonium sulfate, and ion exchange chromatography and gel filtration (Non-patent reference 6).

For a large-scale production of human plasma-derived FVII concentrate, a method for purification from human cryoprecipitate-poor plasma is disclosed that vitamin K dependent coagulation factor rich fraction is first obtained by anion exchange treatment and thereto FVII conformation specific monoclonal antibodies, which can adsorb FVII in the presence of metal ions, are used as an immunosorbent (Non-patent reference 7).

Likewise, a method for preparing FVII and/or FVIIa is disclosed using an absorbent to which human FVII conformation specific monoclonal antibodies are fixed (Patent reference 1). This method, by applying monoclonal antibodies against FVII and/or FVIIa, which distinguish conformational difference due to the presence and absence of the binding of metal cations, to immunosorbent chromatography, allows for the elution and purification of FVII and/or FVIIa of interest without using a powerful denaturant.

Further, it is reported that FVII could be well prepared by a purification method comprising hydrophobic chromatography with Phenyl-Sepharose-HP and gel filtration chromatography with XK26/100 Superose 12, after $Al(OH)_3$ adsorption treatment and ion exchange chromatography with TMAE-EMD and the heating process of lyophilization (Patent reference 2).

PRIOR ART

Patent Reference

Patent reference 1: JP 03-155797 (Japan patent 2824430)
Patent reference 2: JP 2002-518411

Non-Patent Reference

Non-patent reference 1: Hedner, et al., J. Clin. Invest. 71, p. 1836 (1983)
Non-patent reference 2: Peter, W., et al., Blood, 80, p. 25-28, (1992)

Non-patent reference 3: Prydz, J. Scand. J. Clin. Lab. Invest. 1, p. 101 (1964); Gladhaug, A. et al., Biochim. Biophys. Acta 215, p. 105, (1970)

Non-patent reference 4: Laake, K., et al., Thromb. Res. 5, p. 539, (1974); Schiffman, S., et al., Thromb Res. 6, p. 273 (1975)

Non-patent reference 5: Osterud, B., et al., Proc. Natl. Acad. Sci. U.S.A. 74, p. 5260 (1977)

Non-patent reference 6: Broze, Jr. G. J. et al., J. Biol. Chem. 255, p, 1242 (1980)

Non-patent reference 7: Tomokiyo et al., Vox Sanguinis, 2003, 84, p. 54-64

Non-patent reference 8: PRODUCTION OF PLASMA PROTEINS FOR THERAPEUTIC USE p. 68 (2013) by John Wiley & Sons, Inc., Hoboken, N.J.

DISCLOSURE OF THE INVENTION

Technical Problem to be Solved by the Invention

With the conventional methods as described above, although FVII concentrate with high purity can be obtained, a low recovery rate of FVII concentrate from human cryoprecipitate-poor plasma has been a major problem. The reason of this is that FVII has a lower affinity to an anion exchanger as compared to the other similar vitamin K dependent coagulation factors (Non-patent reference 6) and also that FVII has an extremely low concentration in human plasma (Table 1; Non-patent reference 8). It is generally known that human cryoprecipitate-poor plasma has a tendency to solidify when subject to a strong anion exchange resin and this is also one of the reasons of the low recovery rate.

TABLE 1

| Plasma conc. | FII | FVII | FIX | FX |
|---|---|---|---|---|
| µg/mL | 80-90 | 0.4-0.6 | 3-5 | 7-10 |
| nM | 1100-1250 | 8-1.2 | 54-89 | 120-170 |

| Plasma conc. | Protein C | Protein S | Protein Z |
|---|---|---|---|
| µg/mL | 3-5 | 22 | 1.2-2.9 |
| nM | 48-81 | 285 | 19-47 |

What's thought to be the cause of the low recovery rate is that, when FVII is recovered from human plasma through anion exchange resin adsorption, a portion of FVII might be dispensed to a non-adsorption fraction as a consequence of competition with other vitamin K dependent coagulation factors which have a higher affinity to an anion exchanger than that of FVII. In accordance with the method of a large-scale production of Non-patent reference 7, human cryoprecipitate-poor plasma is applied to an anion exchange resin (Q-FF) to adsorb and collect vitamin K dependent coagulation factors including FVII with a recovery rate of FVII being as low as 70%, suggesting that a portion of FVII might remain in a non-adsorption fraction.

Means for Solving the Problems

The present inventors have earnestly studied so as to solve the above problems. As a result, the present inventors have found that FVII and/or FVIIa of interest can be collected with a recovery rate of as high as 90% or more by letting FVII and/or FVIIa which fails to be adsorbed to a first anion exchange resin and remains in a non-adsorption fraction be adsorbed in a second anion exchange resin to thereby complete the present invention.

Thus, the present invention provides a chromatographic method for collecting FVII and/or FVIIa from plasma with a high recovery rate and specifically includes the followings.

[1] A method for purifying blood coagulation factor VII (Factor VII) and/or activated blood coagulation factor VII (activated Factor VII) from plasma-derived fraction, comprising the following steps:
(a) a step of adsorbing Factor VII and/or activated Factor VII to a first anion exchange resin;
(b) a step of adsorbing Factor VII and/or activated Factor VII which remains in a non-adsorption fraction in step (a) to a second anion exchange resin;
(c) a step of recovering Factor VII and/or activated Factor VII from an adsorption fraction in steps (a) and (b).

[2] The method of [1] wherein the steps (a) to (c) allows for collection of Factor VII and/or activated Factor VII from plasma-derived fraction with a yield of 75% or more.

[3] The method of [2] wherein the steps (a) to (c) allows for collection of Factor VII and/or activated Factor VII from plasma-derived fraction with a yield of 90% or more.

[4] The method of any of [1] to [3] wherein the plasma-derived fraction is a cryoprecipitate-poor fraction.

[5] The method of any of [1] to [4] wherein both of the anion exchange resins of (a) and (b) are a strong anion exchange resin.

[6] The method of any one of [1] to [4] wherein the anion exchange resin of (a) is a strong anion exchange resin and the anion exchange resin of (b) is a weak anion exchange resin.

[7] The method of any one of [1] to [4] wherein the anion exchange resin of (a) is a weak anion exchange resin and the anion exchange resin of (b) is a strong anion exchange resin.

[8] The method of any of [1] to [4] wherein both of the anion exchange resins of (a) and (b) are a weak anion exchange resin.

[9] The method of any one of [1] to [4] wherein the anion exchange resins of (a) and (b) are a resin with a positive charge group selected from the group consisting of diethylaminoethyl (DEAE), dimethylaminoethyl (DMAE), trimethylaminoethyl (TMAE), polyethyleneimine (PEI), quaternary aminoalkyl, quaternary aminoethyl (QAE), and quaternary ammonium (Q).

[10] The method of [9] wherein the anion exchange resin of (a) is a resin with diethylaminoethyl (DEAE) and the anion exchange resin of (b) is a resin with quaternary ammonium (Q).

[11] The method of [9] wherein both of the anion exchange resins of (a) and (b) are a resin with quaternary ammonium (Q).

Effects of the Invention

The present invention is a method characterized by that, when plasma-derived fraction is treated with an anion exchange resin, FVII and/or FVIIa which remains in a non-adsorption fraction is collected by treatment with a second anion exchange resin. Since vitamin K dependent coagulation factors other than FVII are removed by the first anion exchange resin treatment, a concentration of FVII and/or FVIIa in proteins present in a non-adsorption fraction relatively increases, allowing efficient collection of FVII and/or FVIIa by the second anion exchange resin treatment.

Also, in accordance with the present invention, tendency of solidification at the time when plasma-derived fraction is treated with an anion exchange resin can be suppressed and FVII and/or FVIIa can be collected from human cryoprecipitate-poor plasma with as high a yield as 90% or more.

BEST MODE FOR CARRYING OUT THE INVENTION

An anion exchange resin as used herein may be either a strong anion exchange resin or a weak anion exchange resin and may be ones where an anion exchange group is introduced onto the surface of a carrier matrix made of any material generally used in the relevant art such as, for instance, natural polymers (cellulose, dextran, agarose) and synthetic polymers (styrene/divinylbenzene copolymer, polyacryl, polyvinyl alcohol, etc.), inorganic material (silica gel, alumina, zirconia), and the like.

An anion exchange group includes, but is not limited to, material having a positive charge group selected from the group consisting of diethylaminoethyl (DEAE), dimethylaminoethyl (DMAE), diethylaminopropyl (DEAP), polyethyleneimine (PEI), quaternary aminoalkyl, trimethylaminoethyl (TMAE), quaternary aminoethyl (QAE), and quaternary ammonium (Q).

An anion exchange group includes strong ones and weak ones. Whether an anion exchange group is strong or weak is determined not by its strength for binding to a protein but by whether its binding with ions is hard to be changed by variation of pHs (strong) or is apt to be effected by variation of pHs (weak).

A strong anion exchanger is the one where an ion exchange capacity does not change even if pH changes. A strong anion exchanger does not receive or lose protons when pH changes and thus keeps a charged condition in a wide pH range. As a strong anion exchanger, TMAE, QAE, Q, PEI and the like are known.

On the other hand, a weak anion exchanger is the one where dissociation degree of an ion exchanger, i.e. an ion exchange capacity, markedly changes depending on pH. A weak anion exchanger receives protons when pH changes and thus an ion exchange capacity varies depending on pH. As a weak anion exchanger, DEAE, DMAE, DEAP and the like are known.

A commercially available anion exchange resin includes, for instance, the followings:

DEAE-Sephacel (registered trademark), DEAE-Sephadex (registered trademark), DEAE-Sepharose CL6B (registered trademark), DEAE-Sepharose Fast Flow (registered trademark), ANX-Sepharose Fast Flow (registered trademark), QAE-Sephadex (registered trademark), Q-Sepharose Fast Flow (registered trademark), Q-Sepharose High Performance (registered trademark), Q-Sepharose Bid Beads (registered trademark) (all from GE Healthcare);

DEAE-Tris-Acryl (registered trademark), DEAE-Spherodex (registered trademark), Q-Hyper-D (registered trademark) (all from Sepracor);

Macroprep DEAE (registered trademark), Macroprep Q (registered trademark) (all from Bio-Rad);

DEAE-Toyopearl (registered trademark), QAE-Toyopearl (registered trademark), Toyopearl Super-Q (registered trademark) (all from Tosoh);

Protein PAK DEAE (Waters);

Fractogel EMD-TMAE (registered trademark), Fractogel END-DEAE (registered trademark), Fractogel EMD-DMAE (registered trademark), Liocrospher 1000 TMAE (registered trademark), Licrospher 1000 DEAE (registered trademark) and Licrospher 4000 DMAE (registered trademark) (all from MERCK-MILLIPORE).

For use in the method according to the present invention, first and second anion exchange resins may be the same or different from each other. Further, several kinds of anion exchange resins may be used in combination depending on selectivity of resins to be used. Besides, a step of adsorption to the first and the second anion exchange resins as used in the present invention may be a column method, a batch method, or a combination of both methods.

A column method is the one where a sample is poured into one end of a column of a long tube (in many cases, glass, plastic such as polypropylene, stainless, etc.) in which an anion exchange resin is charged. On the other hand, a batch method is the one where an anion exchange resin and a sample are put in the same vessel and the mixture is stirred for a fixed period of time. After completion of adsorption, the mixture may be charged in a column for combination with a column method.

The present invention is explained in more detail with the following examples but is not limited thereto.

Example 1

Two-Step Chromatography: Q-Sepharose Fast Flow (Q-FF; Batch Method)→Q-Sepharose Fast Flow (Q-FF; Column Method)

Human cryoprecipitate-poor plasma (24 L; amount of FVII antigen: about 25,000 U) was applied to a first anion exchange resin (Q-FF gel: 0.6 L) (batch method) and the obtained non-adsorption fraction was further applied to a second anion exchange resin (Q-FF gel: 1 L) (column method). The first and the second anion exchange resins were linked together and washed with 10 mM citrate buffer (pH 7; 3 L) comprising 0.2 M sodium chloride and the second anion exchange resin alone was washed with the same buffer (2 L). After washing, the first and the second anion exchange resins were again linked together and elution was conducted with 20 mM citrate buffer (pH 7) comprising 0.7 M sodium chloride.

As a result, a recovery rate of FVII from human cryoprecipitate-poor plasma (a recovery rate of FVII antigen) was 94% after treatment with the two anion exchange resins (Table 3) to achieve a higher recovery rate than that of the prior art (Table 2; Non-patent reference 7). Also, a ratio of FVII antigen amount/total protein amount (a degree of purification) sufficiently increased from that of human plasma (Table 3).

TABLE 2

| Step | Recovery rate (%) of FVII antigen |
|---|---|
| Cryoprecipitate-poor plasma | 100 |
| Q-FF | 70 ± 3.2 (n = 50) |

TABLE 3

| Step | Ratio of FVII antigen amount/total protein amount (U/mg) | Recovery rate (%) of FVII antigen |
|---|---|---|
| Cryoprecipitate-poor plasma | 0.02 ± 0.0006 (n = 6) | 100 |
| Q-FF→Q-FF | 0.79 ± 0.04 (n = 6) | 94 ± 5.3 (n = 6) |

Example 2

Immunoadsorption with Anti-FVII Monoclonal Antibody

The elution fraction from the two-step anion exchange resins (Q-FF→Q-FF) obtained in Example 1 was further applied to anti-FVII conformation specific monoclonal antibody which can adsorb FVII in the presence of calcium ions according to the method of Non-patent reference 7 to purify FVII. As a result, a recovery rate of FVII from human cryoprecipitate-poor plasma was 92% (Table 4) to achieve a higher recovery rate than that of the method of Non-patent reference 7 (Table 5).

TABLE 4

| Step | Recovery rate (%) of FVII antigen |
|---|---|
| Cryoprecipitate-poor plasma | 100 |
| mAb-immobilized gel | 92 ± 11.9 (n = 6) |

TABLE 5

| Step | Recovery rate (%) of FVII antigen |
|---|---|
| Cryoprecipitate-poor plasma | 100 |
| mAb-immobilized gel | 60 ± 2.5 (n = 50) |

Example 3

Two-Step Chromatography: DEAE-Sepharose Fast Flow (DEAE-FF)→Q-Sepharose Fast Flow (Q-FF)

Human cryoprecipitate-poor plasma (3 L; amount of FVII antigen: about 3,000 U) was applied to a first anion exchange resin (DEAE-FF gel: 84 mL) and the obtained non-adsorption fraction was further applied to a second anion exchange resin (Q-FF gel: 135 mL). The first and the second anion exchange resins were linked together and washed with 10 mM citrate buffer (pH 7; 420 mL) comprising 0.2 M sodium chloride and the second anion exchange resin alone was washed with the same buffer (270 mL). After washing, the first and the second anion exchange resins were again linked together and elution was conducted with mM citrate buffer (pH 7) comprising 0.7 M sodium chloride.

As a result, a recovery rate of FVII from human cryocipitate-poor plasma (a recovery rate of FVII antigen) was 95% after treatment with the two anion exchange resins, achieving a higher recovery rate than that of the prior art (Table 2; Non-patent reference 7). Also, a ratio of FVII antigen amount/total protein amount (a degree of purification) sufficiently increased from that of human plasma (Table 6).

TABLE 6

| Step | Ratio of FVII antigen amount/total protein amount (U/mg) | Recovery rate (%) of FVII antigen |
|---|---|---|
| Cryoprecipitate-poor plasma | 0.02 (n = 1) | 100 |
| Q-FF→Q-FF | 0.58 (n = 1) | 95 (n = 1) |

Comparing the two anion exchange resins for a ratio of FVII antigen amount/total protein amount (a ratio of an amount of FVII antigen to an amount of vitamin K dependent coagulation factors) of the respective adsorption fractions when washing and elution were conducted separately with each of the two anion exchange resins, the second anion exchange resin (Q-FF) had extremely higher ratio (Table 7). This result suggested that vitamin K dependent coagulation factors other than FVII were removed by the treatment with the first anion exchange resin (DEAE-FF) to thereby relatively increase a concentration of FVII in vitamin K dependent coagulation factors present in a non-adsorption fraction so as to allow for efficient collection of FVII by the second anion exchange resin treatment.

TABLE 7

| Step | | Amount of FVII antigen (U) | Ratio of FVII antigen amount/total protein amount (U/mg) |
|---|---|---|---|
| DEAE-FF | Adsorption fraction | 4 (n = 1) | 0.004 (n = 1) |
| Q-FF | Adsorption fraction | 2,159 (n = 1) | 0.87 (n = 1) |

INDUSTRIAL APPLICABILITY

The present invention can be used as a method for collecting Factor VII and/or activated Factor VII from plasma-derived fractions.

The invention claimed is:

1. A method for purifying blood coagulation factor VII (Factor VII) and activated blood coagulation factor VII (activated Factor VII) from cryoprecipitate-poor plasma-derived fraction, comprising the following steps:
   (a) applying cryoprecipitate-poor plasma-derived fraction to a first strong anion exchange resin;
   (b) adsorbing Factor VII and activated Factor VII from the cryoprecipitate-poor plasma-derived fraction to the first strong anion exchange resin and recovering a non-adsorbed fraction;
   (c) adsorbing Factor VII and activated Factor VII which remains in the non-adsorbed fraction in step (b) to a second strong anion exchange resin; and
   (d) recovering Factor VII and activated Factor VII from first and second strong anion exchange resins in steps (b) and (c), by elution wherein recovering Factor VII and activated Factor VII from the first strong anion exchange resin and second strong anion exchange resin occurs simultaneously.

2. The method of claim 1 wherein the steps (a) to (d) allow for collection of Factor VII and activated Factor VII from cryoprecipitate-poor plasma-derived fraction with a yield of 75% or more.

3. The method of claim 2 wherein the steps (a) to (d) allow for collection of Factor VII and activated Factor VII from cryoprecipitate-poor plasma-derived fraction with a yield of 90% or more.

4. The method of claim 1 wherein the strong anion exchange resins of (b) and (c) are a resin selected from the group consisting of trimethylaminoethyl (TMAE), polyethyleneimine (PEI), quaternary aminoalkyl, quaternary aminoethyl (QAE), and quaternary ammonium (Q).

5. The method of claim 4 wherein both of the strong anion exchange resins of (b) and (c) are a resin with quaternary ammonium (Q).

* * * * *